(12) United States Patent
Jones

(10) Patent No.: US 9,011,372 B2
(45) Date of Patent: Apr. 21, 2015

(54) MANUAL BREAST PUMP WITH RESILIENT RETURN

(75) Inventor: Jason Donald Jones, Centerville, OH (US)

(73) Assignee: Platinum Products Holding, Inc., Lincolnshire, IL (US)

( * ) Notice: Subject to any disclaimer, the term of this patent is extended or adjusted under 35 U.S.C. 154(b) by 236 days.

(21) Appl. No.: 12/855,330

(22) Filed: Aug. 12, 2010

(65) Prior Publication Data

US 2012/0022445 A1  Jan. 26, 2012

Related U.S. Application Data

(60) Provisional application No. 61/366,645, filed on Jul. 22, 2010.

(51) Int. Cl.
*A61M 1/06* (2006.01)

(52) U.S. Cl.
CPC .......................................... *A61M 1/06* (2013.01)

(58) Field of Classification Search
CPC ....... A61M 1/06; A61M 1/062; A61M 1/064; A61M 1/066; A61M 1/068; A61J 9/00
USPC ...................................................... 604/74–76
See application file for complete search history.

(56) References Cited

U.S. PATENT DOCUMENTS

| | | | |
|---|---|---|---|
| 4,323,067 A | 4/1982 | Adams | |
| 4,573,969 A | 3/1986 | Schlensog et al. | |
| 4,705,504 A | 11/1987 | Viers | |
| 4,772,262 A | 9/1988 | Grant et al. | |
| 4,784,175 A | 11/1988 | Hicks | |
| 4,813,932 A | 3/1989 | Hobbs | |
| 4,892,517 A | 1/1990 | Yuan et al. | |
| D309,500 S | 7/1990 | Yuan et al. | |
| 5,007,899 A | 4/1991 | Larsson | |
| 5,415,632 A * | 5/1995 | Samson | ........................... 604/74 |
| 5,542,921 A | 8/1996 | Meyers et al. | |
| 5,749,850 A * | 5/1998 | Williams et al. | ................. 604/74 |
| 5,885,246 A | 3/1999 | Ford | |
| 5,941,847 A | 8/1999 | Huber et al. | |
| 5,993,479 A | 11/1999 | Prentiss | |
| 6,090,065 A | 7/2000 | Giles | |
| 6,440,100 B1 | 8/2002 | Prentiss | |
| 6,461,324 B1 | 10/2002 | Schlensog | |
| 6,579,258 B1 | 6/2003 | Atkin et al. | |
| 6,705,920 B1 | 3/2004 | Engel | |
| 6,723,066 B2 | 4/2004 | Larsson et al. | |
| 7,396,340 B2 | 7/2008 | Onuki et al. | |
| 7,413,557 B2 | 8/2008 | Samson et al. | |
| D583,985 S | 12/2008 | Warden et al. | |
| 7,824,363 B2 | 11/2010 | Myers | |
| 2001/0038799 A1 | 11/2001 | Silver et al. | |
| 2001/0044593 A1 | 11/2001 | Lundy | |

(Continued)

*Primary Examiner* — Bhisma Mehta
*Assistant Examiner* — Jenna Zhang
(74) *Attorney, Agent, or Firm* — Benesch Friedlander Coplan Aronoff LLP

(57) ABSTRACT

A manual breast pump comprising a pump housing defining an inlet orifice, an outlet orifice, and a pump orifice all in fluid communication with one another, the pump housing including a pump chamber, a repositionable actuator disposed within the pump chamber and repositionable within the pump chamber between a retracted position and an extended position, and a resilient band concurrently mounted to the pump housing and operatively mounted to the repositionable actuator.

16 Claims, 6 Drawing Sheets

(56) References Cited

U.S. PATENT DOCUMENTS

| | | |
|---|---|---|
| 2002/0072701 A1 | 6/2002 | Nuesch |
| 2003/0153869 A1 | 8/2003 | Ytteborg |
| 2003/0191433 A1 | 10/2003 | Prentiss |
| 2004/0249340 A1* | 12/2004 | Britto et al. ............ 604/74 |
| 2005/0015045 A1* | 1/2005 | Tashiro et al. ........... 604/74 |
| 2005/0154349 A1 | 7/2005 | Renz et al. |
| 2008/0039781 A1 | 2/2008 | Bjorge |
| 2008/0208115 A1* | 8/2008 | Kliegman et al. ........ 604/74 |

* cited by examiner

SECTION A-A

MANUAL BREAST PUMP WITH RESILIENT RETURN

CROSS REFERENCE TO RELATED APPLICATIONS

The present application claims the benefit of U.S. Provisional Patent Application Ser. No. 61/366,645, entitled, "MANUAL BREAST PUMP WITH RESILIENT RETURN," filed Jul. 22, 2010, the disclosure of which is incorporated herein by reference.

INTRODUCTION TO THE INVENTION

The present disclosure is directed to breast pumps and, specifically, to manual breast pumps having an automatic return using a resilient return.

DETAILED DESCRIPTION

Figure 1:
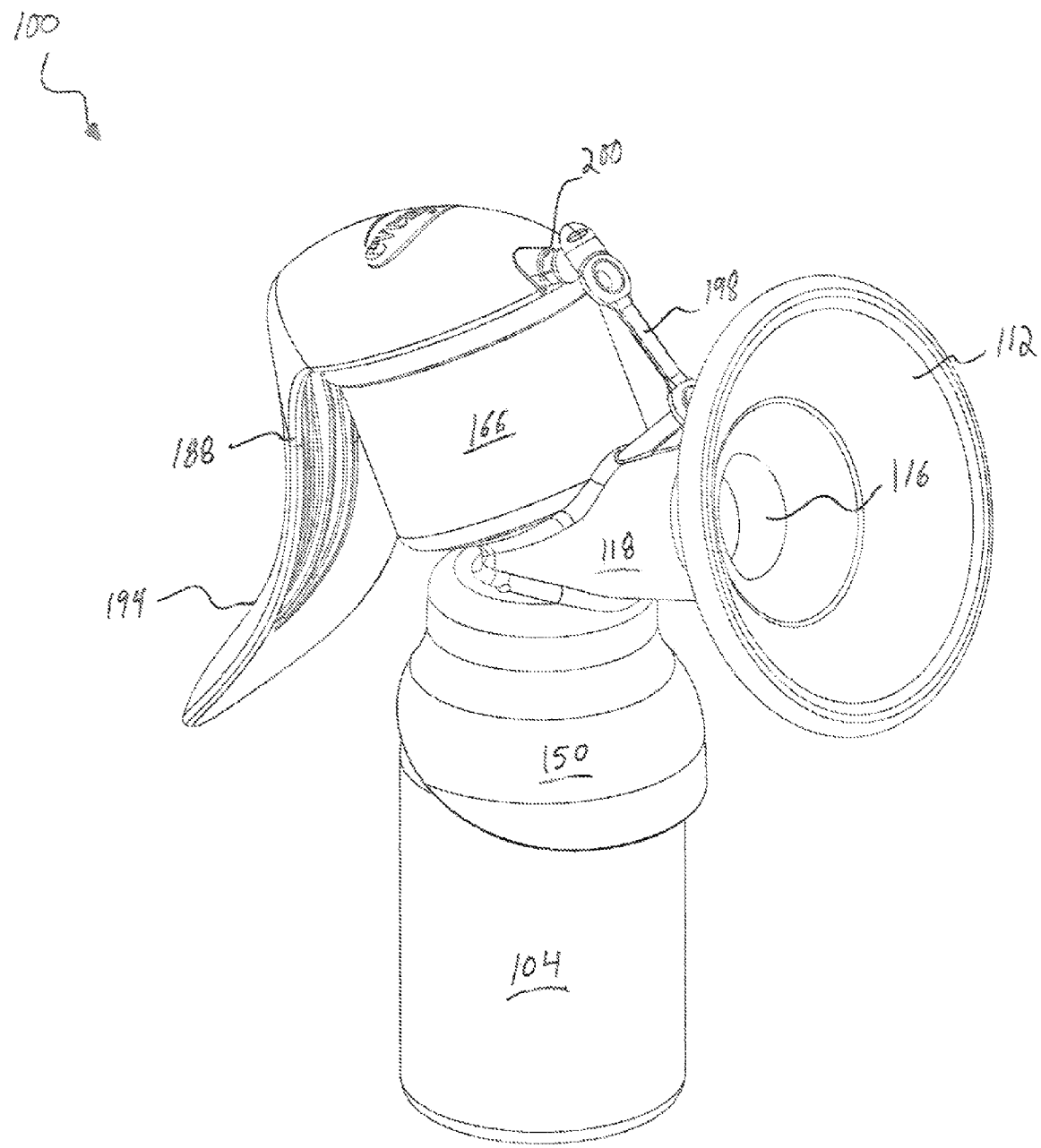
FIG. 1 is an elevated perspective view of an exemplary breast pump in accordance with the instant disclosure.
Figure 2:
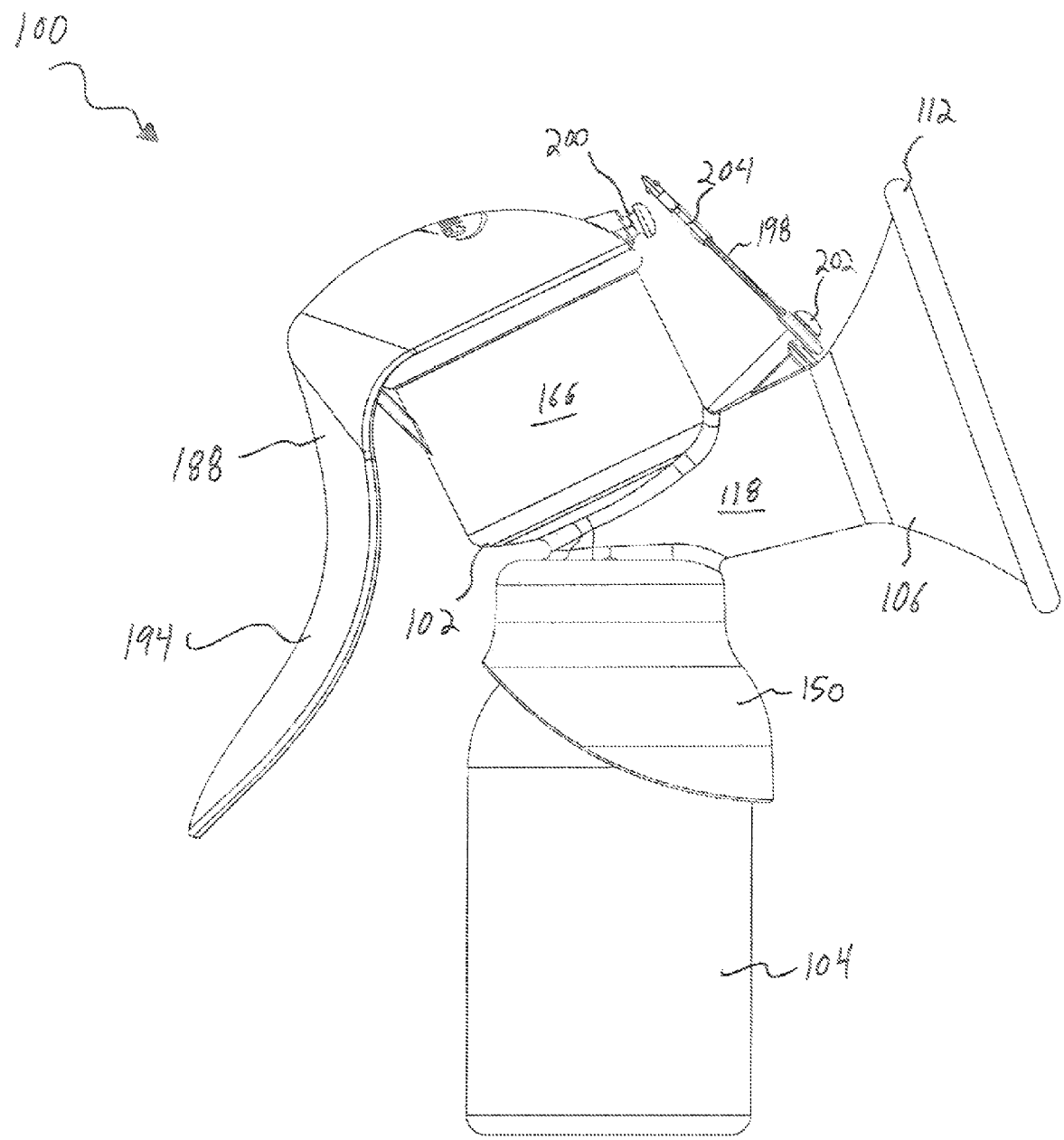
FIG. 2 is a right side, profile view of the exemplary breast pump of FIG. 1.
Figure 3:
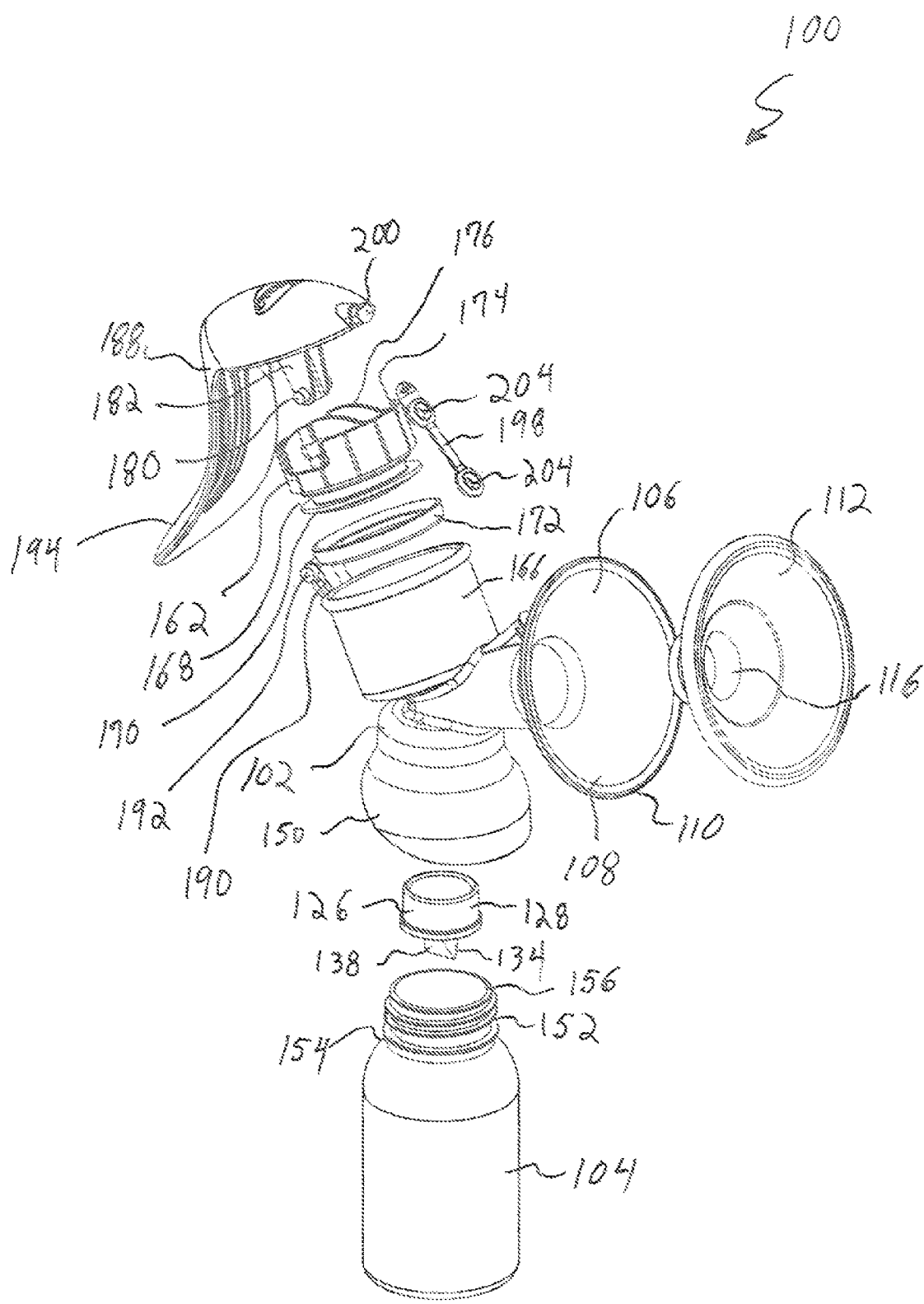
FIG. 3 is an exploded view of the exemplary breast pump of FIG. 1.
Figure 4:
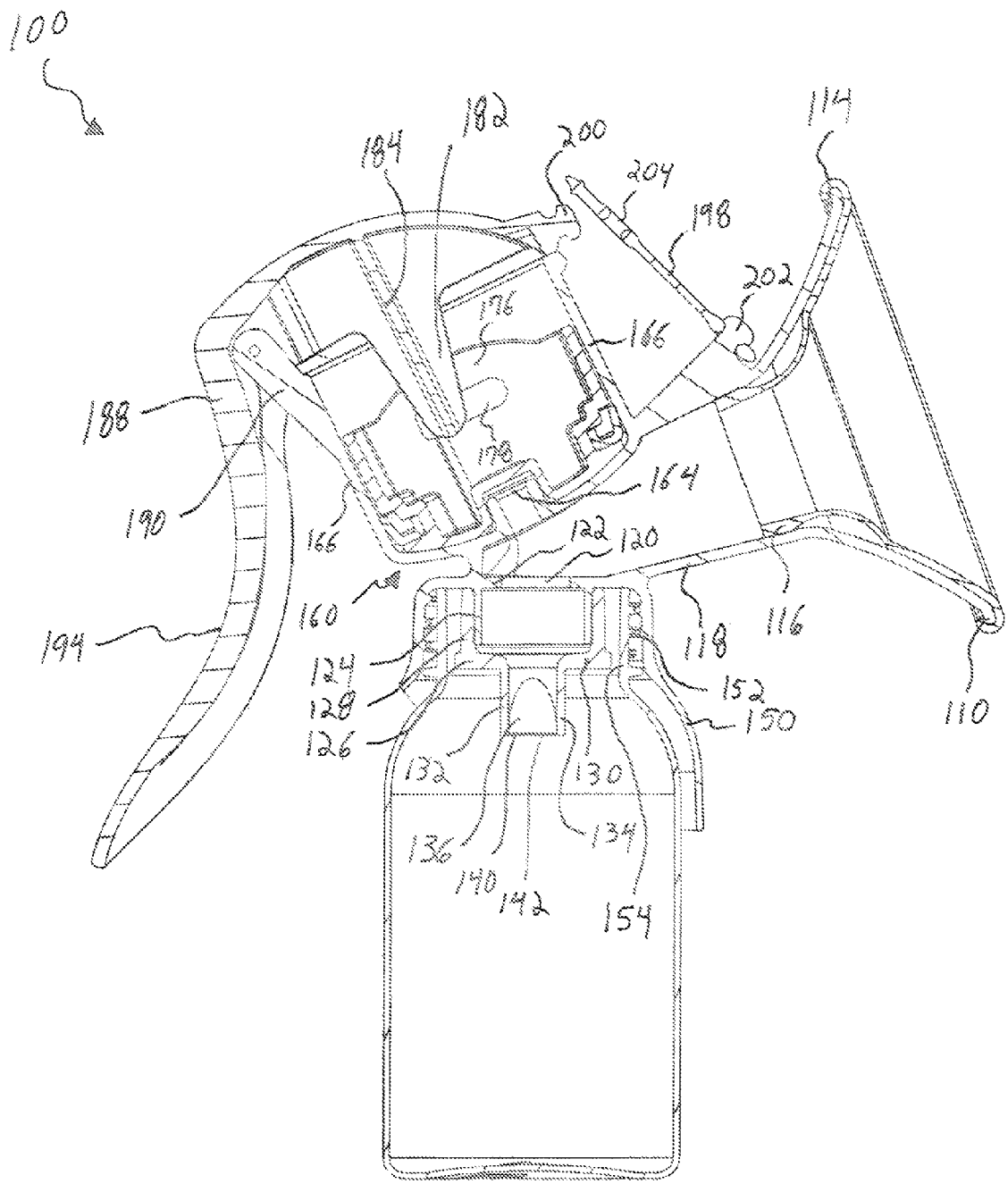
FIG. 4 is a cross-sectional view of the exemplary breast pump of FIG. 2 taken along a midline plane.

The exemplary embodiments of the present invention are described and illustrated below to encompass manual breast pump devices and methods of operating and assembling a manual breast pump. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-4, an exemplary breast pump 100 includes a primary housing 102 that connects to a milk reservoir bottle 104 in order to store milk withdrawn from a woman's breast. The primary housing 102 includes a funnel 106 having a generally circular cross-section that is hollow and defines an enclosed fluid path for the milk to travel and ultimately be deposited in the bottle 104. In exemplary form, the funnel 106 decreases in diameter as the distance from the mouth 108 increases. Proximate the mouth 108, the funnel 106 includes a circular flange 110 that provides a foothold for an elastomeric insert 112 that is seated within the funnel. This elastomeric insert 112 is also funnel-shaped to generally match the interior topography of funnel 106, but includes a distal lip 114 that includes a circumferential cavity that receives the circular flange 110. In this manner, the lip 114 wraps around the flange 110 to secure the insert 112 to the funnel 106. But the insert 112 is also mounted to the funnel 106 by a compression fit formed between a proximal portion 116 of the insert and the funnel. Specifically, the proximal portion 116 includes a circular cross-section having a smooth external diameter that is slightly larger than the corresponding internal smooth diameter of the funnel 106. Accordingly, when the proximal portion 116 is inserted fully into the funnel 106, the proximal portion is in compression and this creates a compression fit to also secure the insert 112 to the funnel.

A proximal portion 118 of the funnel 106 is constricted to direct milk through a central orifice 120 that is recessed below the mouth 108 of the funnel 106. The central orifice 120 is defined by a circumferential flange 122 that extends perpendicularly from a cylindrical wall 124. The cylindrical wall 124 defines a hollow, cylindrical conduit in selective communication with the interior of the bottle 104. The selective communication occurs, in part, from an elastomeric valve 126 that circumscribes the cylindrical wall 124 to form a seal between the valve and cylindrical wall. The valve 126 includes a cylindrical wall 128 that joins a perpendicular wall 130 and transitions into a bounded conduit 132. The bounded conduit 132 includes a cylindrical wall 134 that joins two planar walls 136, 138 in order to taper the bounded conduit into a V-shaped profile at one end 140. But this V-shaped profile is not a true V-shape because the end 140 does not include a rigid connection between the planar walls. Rather, the planar walls are not continuously, rigidly joined at the end 140 because of a horizontal slit 142. This horizontal slit 142 allows milk to pass therethrough and into the interior of the bottle 104. As will be discussed in more detail hereafter, operation of the pump mechanism is operative to selectively force the two planar walls 136, 138 against one another at the end 140 to effectively close off communication through the slit 142 with the piston is retracted.

In order to couple the primary housing 102 to the milk reservoir bottle 104, the housing includes a shroud 150 that covers the top of the bottle. Specifically, the interior of the shroud 150 is threaded to mate with threads 152 on the exterior of the bottle neck 154 so that twisting of the bottle 106 with respect to the housing 102 is operative to engage and disengage the bottle from the housing. The bottle neck 154 is generally circular in horizontal cross-section and includes a generally planar upper, circumferential surface 156 that contacts a generally planar, upper interior surface of the shroud 150 in order to form a seal between the housing 102 and the bottle 104 when the bottle is fully secured to the housing.

In order to withdraw milk from a woman's breast, the exemplary breast pump 100 creates an area of lower pressure proximate the breast using a pump mechanism 160. The pump mechanism 160 includes a repositionable piston 162 that draws in air through an orifice 164 and into a cavity of the housing that is defined by a cylindrical wall 166. By drawing air from the funnel 106 and through the orifice 164 while the woman's breast is sealed against the elastomeric insert 112, a lower pressure area proximate the woman's breast is created. In order to draw in air from within the funnel 106, the piston 162 is vertically repositionable within the cylindrical wall 166 away from the orifice 164 (i.e., retracted).

The piston 162 includes a circumferential recess 168 proximate its distal end 170 that receives a piston ring 172 in order to form a seal between the piston and cylindrical wall 166. In this exemplary embodiment, the piston ring is a resilient material such as, without limitation, natural rubber, synthetic rubber, and other elastomeric materials. A proximal end 174 of the piston includes a pair of parallel, vertical walls 176 that each include an elongated through opening 178. This elongated through opening 178 receives a solid, cylindrical projection 180 extending from opposite sides of a pair of vertical walls 182 that are spaced apart by perpendicular vertical wall 184 mounted to a handle 188. Each of the three vertical walls 182, 184 extend from the roof 186 of the handle 188, where the handle is pivotally mounted to the primary housing 102. Specifically, the primary housing 102 includes an appendage 190 extending from the exterior of the cylindrical wall 166, opposite the funnel 106. The appendage 190 includes a pair of solid cylindrical projections 192 extending from opposite sides, proximate the top of the appendage. In exemplary form, the solid cylindrical projections 192 are received within corresponding cavities formed within the interior of the handle 188 so that the handle pivots about the solid cylindrical projections when actuated.

In order to actuate the handle 188, a user pushes against the curved, exterior portion 194 of the handle so that that the handle pivots on the solid cylindrical projections 192. As the handle 188 is pivoted by pushing on the curved, exterior portion 194 and directing it toward the bottle 104, the solid, cylindrical projection 180 extending from opposite sides of a pair of vertical walls 182 are repositioned along an arcuate path. This arcuate path allows the solid, cylindrical projections 180 to be repositioned within the elongated through opening 178 and correspondingly retract the piston 162 and piston ring 172 within the interior of the cylindrical wall 166. While the handle 188 is pivoted to retract the piston 162 and piston ring 172 within the interior of the cylindrical wall 166, an elastic strap 198 is concurrently being stretched between a first mounting fixture 200 at the front, top portion of the handle and a second mounting fixture 202 located at the top of the funnel 106.

The elastic strap 198 includes two through holes 204 that are spaced apart from one another. Each hole 204 is adapted to receive one of the two mounting fixtures. The profile of the hole is inversely hourglass shaped so the hole diameter narrows from both the top and bottom to a minimum at the middle of the hole, in a vertical direction. In this exemplary embodiment, the mounting fixtures 200, 202 each comprise a rounded, hourglass shaped projection. The rounded nature of the mounting fixtures 200, 202 allows the elastic strap 198 to be stretched so that the holes 204 are deformed to accommodate throughput of the ends of the mounting fixtures. After the holes 204 are deformed and the mounting figures extend through the holes, the holes are then relaxed so that the narrow part of the hourglass shape is where the strap 198 is seated to mount the strap to the mounting fixtures 200, 202.

When the elastic strap 198 is concurrently mounted to the handle 188 and housing 106, the elastic strap 198 provides resistance to the pivoting movement of me handle 188 and thus the retraction of the piston 162. So when the user is no longer applying a sufficient force to the handle 188 pushing it toward the bottle 104, the elasticity of the strap 198 causes the handle 188 to be pulled away from the bottle and, thus, pulls the piston 162 and piston ring 172 toward the orifice 164.

The components of the foregoing exemplary breast pump 100 may be fabricated from various materials. For example, the housing 102 may be fabricated from a polymer. The handle 188 may also be fabricated from a polymer. And so too can the bottle 108 be fabricated from a polymer. Obviously, the strap 198 is preferably fabricated from a resilient material such as an elastomer. By way of example, the strap 198 may be fabricated from natural rubber, silicone rubber, and/or latex. But it should be understood that different materials may be utilized and still fall within the scope of the invention such as, without limitation, ceramics, glass, and metals.

Figure 5:
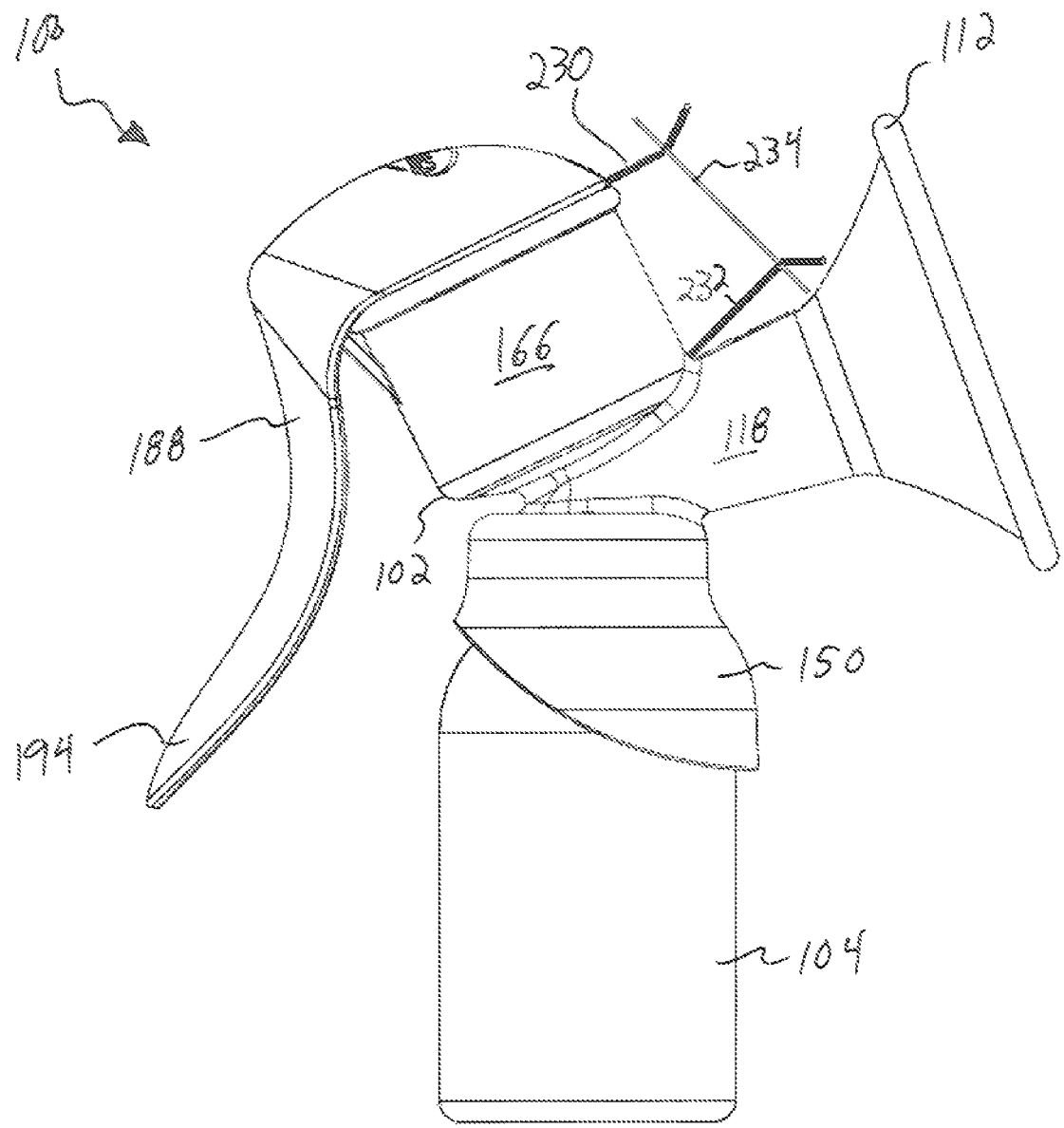
FIG. 5 is a right side, profile view of an alternate exemplary breast pump.

Referring to FIG. 5, while the foregoing exemplary breast pump 100 has been described using mounting fixtures 200, 202 that each comprise a rounded, hourglass shaped projection, it is also within the scope of the disclosure to use differently shaped mounting fixtures 230, 232. For example, the mounting fixtures 230, 232 may comprise a pair of J-shaped projections that are oriented in parallel to provide a gap therebetween. Depending upon the angle, size, and spacing of the J-shaped projections, one or both projections 230, 232 may be received through corresponding holes 204 in the strap 198. In this alternate exemplary configuration, the J-shaped projections 230 extend from a front, top portion of the handle 188 with the end of the J-shaped projections extending upward, whereas another pair of J-shaped projections 232 extend from the top of the funnel 106 so that the ends of the projection do not extend upward. And the alternate mounting fixtures 230, 232 may also accommodate an alternate strap 234.

Figure 6:
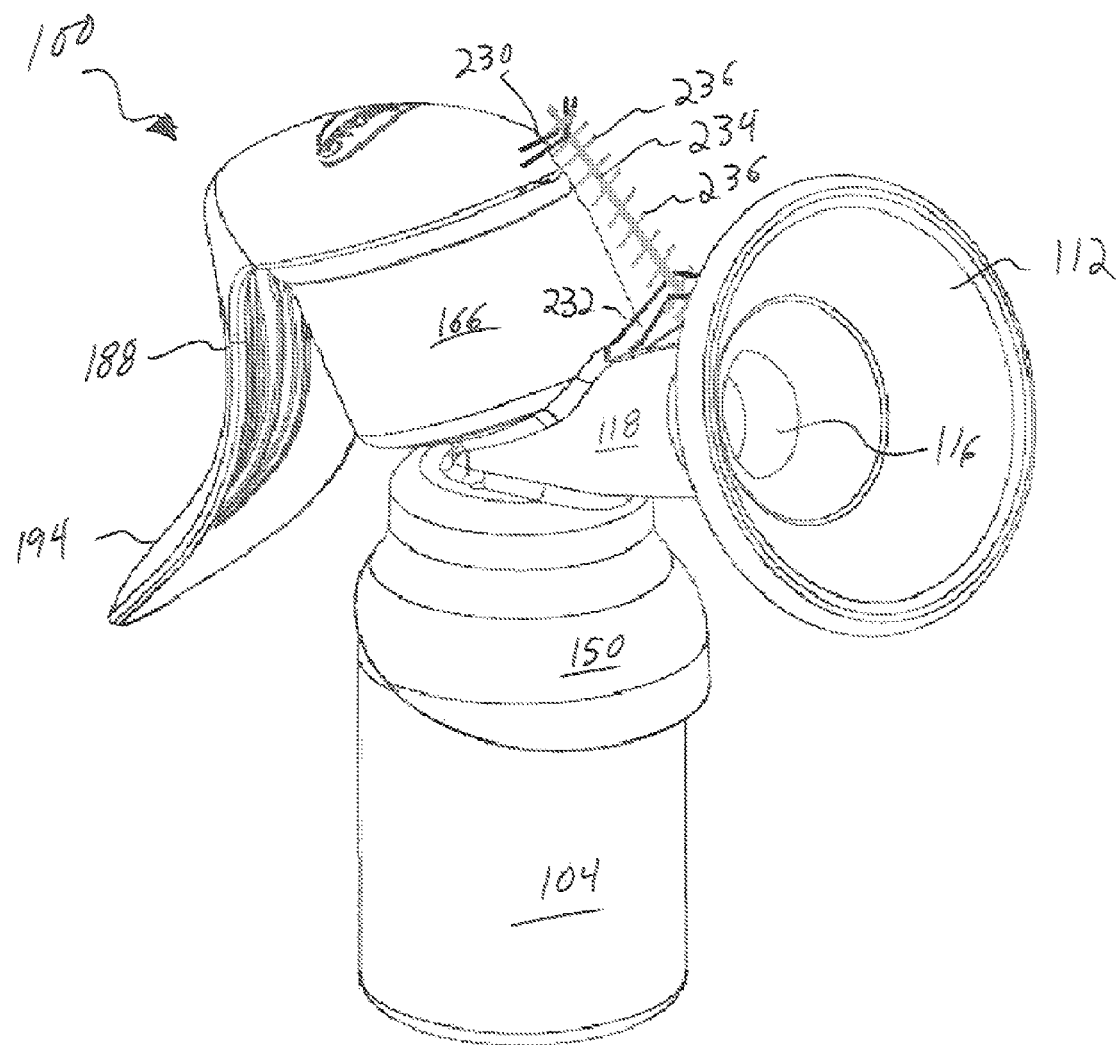
FIG. 6 is an elevated perspective view of the alternate exemplary breast pump of FIG. 5.

As shown in FIGS. 5 and 6, this alternate strap 234 is adapted for use with the alternate mounting fixtures 230, 232. In exemplary form, the alternate strap 234 is also at least partially elastic and includes a series of transverse lengths 236 that intersect the primary longitudinal aspect of the strap 234 at generally right angles. The transverse lengths 236 are generally evenly spaced apart. Once the strap 234 is stretched to be taught and a corresponding transverse length 236 is captured by each of the mounting fixtures 230, 232, the strap is securely mounted to the handle 188 and the primary housing 102. In this manner, the alternate strap 234 provides generally the same functionality as the primary strap 198

It is also to be understood that while the foregoing embodiment and alternate embodiment have been described using components of a piston pump, it is also within the scope of the invention to utilize components of a diaphragm pump.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A manual breast pump comprising:
    a primary housing defining an inlet orifice, a central orifice, an a pump orifice all in fluid communication with one another, the primary housing including a pump chamber and a funnel;
    a repositionable actuator disposed within the pump chamber and repositionable within the pump chamber between a retracted position and an extended position;
    a handle including a handle protrusion, wherein the handle is pivotably mounted to the primary housing and capable of moving the repositionable actuator from the retracted position to the extended position;
    a resilient strap comprising a first end and a second end, wherein the strap is mounted to the handle at the first end and to the primary housing at the second end; and
    wherein the resilient strap further includes an opening through the first end that is configured to receive at least a portion of the handle protrusion to mount the resilient strap to the handle.

2. The manual breast pump of claim 1, wherein the resilient strap is positioned external to the primary housing.

3. The manual breast pump of claim 1, wherein the funnel comprises a hollow conical section having an interior that at least partially defines the central orifice and the pump orifice.

4. The manual breast pump of claim 3, wherein the pump orifice overlies the central orifice.

5. The manual breast pump of claim 1, further comprising an elastomeric valve mounted to the primary housing and located downstream from the central orifice.

6. The manual breast pump of claim 5, wherein the elastomeric valve comprises a cylindrical wall that circumscribes a cylindrical wall of the primary housing to form a compression fit to mount the elastomeric valve to the primary housing.

7. The manual breast pump of claim 5, wherein:
the elastomeric valve comprises a bounded conduit defined by a cylindrical valve wall, a first planar wall, and a second planar wall; wherein the first planar wall and the second planar wall converge proximate an end of the elastomeric valve to form a slit that is configured to selectively open and close the end of the valve.

8. The manual breast pump of claim 1, further comprising a reservoir bottle mounted to the primary housing.

9. The manual breast pump of claim 8, further comprising an elastomeric valve mounted to the primary housing and located downstream from the central orifice.

10. The manual breast pump of claim 1, wherein:
the repositionable actuator includes a piston comprising an elongated opening configured to receive a projection disposed on the handle.

11. The manual breast pump of claim 1, wherein:
the repositionable actuator includes a piston,
the handle includes an elongated opening; and,
the piston includes a projection that is capable of being received by the elongated opening.

12. The manual breast pump of claim 1, wherein:
the repositionable actuator includes a piston,
the pump chamber is partially defined by a circumferential wall that provides a linear travel path for the piston.

13. The manual breast pump of claim 1, wherein:
the handle has an S-shaped profile and the protrusion has an hourglass-shaped profile.

14. The manual breast pump of claim 1, wherein:
the primary housing includes a housing protrusion; and,
the resilient strap includes a second opening through the second end that is configured to receive at least a portion of the housing protrusion to mount the resilient strap to the primary housing.

15. The manual breast pump of claim 1, wherein:
the repositionable actuator includes a piston: and,
the piston includes a circumferential recess that is configured to receive an elastomeric piston ring.

16. The manual breast pump of claim 1, wherein the repositionable actuator includes a diaphragm.

* * * * *